United States Patent [19]

Irie et al.

[11] Patent Number: 5,264,495
[45] Date of Patent: Nov. 23, 1993

[54] METHOD FOR PRODUCTION OF SALT-RESISTANT ABSORBENT RESIN

[75] Inventors: Yoshio Irie; Katsuhiro Kajikawa; Hitoshi Takahashi, all of Himeji; Teruaki Fujiwara, Nagaokakyo, all of Japan

[73] Assignee: Nippon Shokubai Kagaku Kogyo Co., Ltd., Osaka, Japan

[21] Appl. No.: 691,820

[22] Filed: Apr. 26, 1991

[30] Foreign Application Priority Data

Apr. 27, 1990 [JP] Japan ................................ 2-110089

[51] Int. Cl.$^5$ .................... C08F 265/02; C08F 267/02
[52] U.S. Cl. .................................. 125/301; 125/302; 125/305; 125/308; 521/149
[58] Field of Search ............... 525/301, 302, 305, 308; 521/149

[56] References Cited

U.S. PATENT DOCUMENTS

| | | | |
|---|---|---|---|
| 3,661,815 | 5/1972 | Smith | 525/54.32 |
| 4,076,663 | 2/1978 | Masuda | 525/54.32 |
| 4,102,842 | 7/1978 | Fujimoto | 524/555 |
| 4,286,082 | 8/1981 | Tsubakimoto et al. | 526/240 |
| 4,666,983 | 5/1987 | Tsubakimoto et al. | 525/119 |

FOREIGN PATENT DOCUMENTS

| | | |
|---|---|---|
| 2305452 | 3/1976 | France . |
| 54-20093 | 2/1979 | Japan . |
| 55-84304 | 6/1980 | Japan . |
| 56-161412 | 12/1981 | Japan . |
| 61-36309 | 2/1986 | Japan . |
| 61-130324 | 6/1986 | Japan . |

OTHER PUBLICATIONS

Database WPIL, No. 86-160317, Derwent Pubs., Ltd., London, GB; & JP-A-61,094,655, May 13, 1986 (Miyata N).

*Primary Examiner*—Morton Foelak
*Assistant Examiner*—D. Truong
*Attorney, Agent, or Firm*—Burns, Doane, Swecker & Mathis

[57] ABSTRACT

A method for the production of a salt-resistant absorbent resin, which comprises subjecting an aqueous solution of at least one monomer component (A) selected from the group consisting of unsaturated carboxylic acids and salts thereof to aqueous solution polymerization in the presence of from 1 to 30 parts by weight, based on 100 parts by weight of said monomer component (A), of an absorbent resin (B).

20 Claims, No Drawings

METHOD FOR PRODUCTION OF SALT-RESISTANT ABSORBENT RESIN

BACKGROUND OF THE INVENTION

1. Field of the Invention

This invention relates to a method for the production of a salt-resistant absorbent resin. More particularly, it relates to a method for the production of an absorbent resin possessing high gel strength and improved salt-resistance.

2. Description of the Prior Art

The absorbent resins have been heretofore utilized in various absorbent materials represented by disposable diapers, sanitary articles, water-retaining agents for soil, and sealing materials.

These absorbent resins are broadly divided into those of the type possessing such an electrolytic structure as a carboxyl group and those of the type possessing a nonionic hydrophilic segment. As the absorbent resins of the former type, cross-linked acrylic acid (salt) polymer [JP-A-55-84,304(1980)], hydrolyzed starch-acrylonitrile graft copolymer (U.S. Pat. No. 3,661,815), neutralized starch-acrylic acid graft copolymer (U.S. Pat. No. 4,076,663), and saponified acrylic ester-vinyl acetate copolymer (U.S. Pat. No. 4,102,842), for example, have been known. As the absorbent resins of the latter type, modified cross-linked polyvinyl alcohol [JP-A-54-20,093(1979)] and partially cross-linked polyethylene oxide [JP-A-61-1309324(1986)], for example, have been known.

The absorbent resins by nature have found utility in a wide range of industrial fields in need of them for the purpose of absorbing various aqueous solutions. But their absorbency varies to a large extent by the kinds of liquids to be absorbed. When they are used in disposable diapers, for example, their absorbency are varied by changes in salt concentration of urine and diaper qualities are consequently also varied. Their absorbency is affected by the salt concentration, so there are times when these absorbent resins find restricted utility in the field of agriculture and horticulture or in the application to water-repellent agents.

The absorbent resins of the type possessing an electrolytic structure such as a carboxyl group, for example, generally possess high gel strength and exhibit a very high absorbency as to deionized water. They, however, have the problem of poor resistance to salts as evinced by their notably low absorbency exhibited to electrolytic solutions such as an aqueous common salt solution.

The absorbent resins of the latter type possessing a nonionic hydrophilic segment are excellent in terms of salt-resistance as evinced by small decreases in their absorbency exhibited to electrolytic solutions. They, however, possess weak gel strength, betray low speeds of absorption, and show only low absolute values of absorbency.

As an excellent salt-resistant resin the absorbent resin incorporating therein a sulfonic acid group which is a strong electrolyte [JP-A-61-36,309(1986) and JP-A-56-161,412(1981)] has been known. Though this resin manifests an outstanding resistance to liquids containing polyvalent ions, it is as deficient in salt-resistant ability in liquids containing monovalent ions. Moreover, this resin is expensive because it uses as a raw material a monomer possessing a sulfonic acid group.

An object of this invention, therefore, is to provide a method for the production of a salt-resistant absorbent resin.

Another object of this invention is to provide a method for inexpensive production of an absorbent resin possessing high gel strength and yielding very slightly to variation in absorbency due to the salt concentration in an aqueous solution subjected to absorption.

SUMMARY OF THE INVENTION

The objects described above are accomplished by a method for the production of a salt-resistant absorbent resin, which method comprises subjecting an aqueous solution of at least one monomer component (A) selected from the group consisting of unsaturated carboxylic acids and salts thereof to aqueous solution polymerization in the presence of from 1 to 30 parts by weight, based on 100 parts by weight of the monomer component (A), of an absorbent resin (B).

The salt-resistant absorbent resin obtained by the method of production according with this invention preeminently excels in both salt-resistance and gel strength. In the present invention, the portion of the salt-resistant absorbent resin obtained by this invention which has a particle size in a specific range may be used as the absorbent resin (B). When the portion of the resin having a fine range of particle sizes is used as the absorbent resin (B), for example, the produced salt-resistant absorbent resin has a notably decreased content of minute particles of not more than 149 mm in diameter and excels in economy and in various absorption properties as well. When this product is used in the fabrication of various absorbent articles such as disposable diaper and sanitary cotton, it precludes the otherwise inevitable diffusion of fine dust in the ambient air and consequently enjoys the advantage of eliminating the problem of labor hygiene. By making the most of these characteristic features, the salt-resistant absorbent resin obtained by this invention can be used effectively in disposable diapers, sanitary articles, sealing materials for agriculture and horticulture, slip additives for propulsion techniques, agents for preventing leakage of soil in ground excavation, setting agents for sludge, carpet cushions, and coating agents for agriculture, for example.

The unsaturated carboxylic acids to be used in this invention include (meth)acrylic acids, crotonic acid, itaconic acid, maleic acid, fumaric acid, and citraconic acid, for example. The unsaturated carboxylates which are similarly usable include alkali metal salts, ammonium salts, and substituted ammonium salts of the acids enumerated above, for example. These unsaturated carboxylic acids and salts thereof mentioned above may be used either singly or in the form of a combination of two or more members.

In order for the produced absorbent resin to acquire excellent salt-resistance, it is preferable to use acrylic acid and/or acrylic acid salts as an essential component of the unsaturated carboxylic acid and/or the salts thereof. It is especially preferable to use a combination of from 10 to 70 mol%, preferably from 20 to 40 mol%, of acrylic acid and from 90 to 30 mol%, preferably from 80 to 60 mol%, of acrylic acid salts.

The monomer component (A), when necessary, may incorporate therein another unsaturated monomer in addition to the aforementioned unsaturated carboxylic acid and/or salt thereof.

The other unsaturated monomers which are usable for this additional use in the monomer component (A) include unsaturated sulfonic acids such as 2-(meth)acrylamide-2-methylpropane sulfonic acids, vinyl sulfonic acid, (meth)allyl sulfonic acid, styrene sulfonic acid, sulfoethyl(meth)acrylates, sulfopropyl(meth)acrylates, and vinyl toluene sulfonic acid and salts thereof; unsaturated amine compounds such as N,N-dimethylaminoethyl(meth)acrylates and N,N-diethylaminoethyl(meth)acrylates and quaternary salts thereof; (meth)acrylic esters such as hydroxyethyl(meth)acrylates, methoxyethyl(meth)acrylates, hydroxypropyl(meth)acrylates, polyethylene glycol mono(meth)acrylates, polypropylene glycol mono(meth)acrylates, methoxypolyethylene glycol mono(meth)acrylates, methoxypolypropylene glycol mono(meth)acrylates, methyl (meth)acrylates, and ethyl (meth)acrylates; unsaturated amides such as (meth)acrylamides, N-hexyl(meth)acrylamides, N-methylol(meth)acrylamides, and N,N-dimethyl(meth)acrylamides; styrenes and derivatives thereof such as styrene, a-methyl styrene, o-methyl styrene, and p-methyl styrene; and (meth)acrylonitriles, and vinyl acetate, for example. One member or a combination of two or more members selected from the group enumerated above may be used in an amount of less than 50% by weight, preferably less then 40% by weight, in the monomer component (A).

The absorbent resin (B) to be used in this invention has no particular restriction except for the sole requirement that it should be a water-insoluble resin capable of forming a hydrated gel on absorption of water. The absorbent resins which fulfill this requirement include cross-linked carboxymethyl cellulose, modified cross-linked polyvinyl alcohol, cross-linked isobutylene-maleic anhydride copolymer, saponified cross-linked acrylic ester-vinyl acetate copolymers, partially cross-linked polyethylene oxide, hydrolyzed cross-linked starch-acrylonitrile graft copolymer, neutralized starch-acrylic acid graft copolymer, and cross-linked partially neutralized (meth)acrylic acid polymers, for example.

Among other absorbent resins cited above, the cross-linked partially neutralized (meth)acrylic acid polymers prove to be particularly preferable. For example, the absorbent resins possessing capacities for absorption ranging from 100 to 1,000 times the original volume which are disclosed in JP-A-56-93,716(1981), EP-B-0036463, JP-A-56-147,806(1981), U.S. Pat. No. 4,552,938, EP-B-0083022, U.S. Pat. No. 4,093,773, U.S. Pat. No.4,155,893, JP-B-53-46,200(1979), and U.S. Pat. No. 4,041,228 are favorably usable as the absorbent resin (B) in this invention. Particularly for the purpose of enabling the absorbent resin (B) to swell by uniformly absorbing the monomer component, assume an IPN structure, induce grafting efficiently, and ensure production of an excellent salt-resistant absorbent resin, this absorbent resin (B) is preferable to be in the form of powder having a water content in the range of from 0.1 to 10% by weight. For the purpose of quickly inducing the absorption of the monomer component (A), the absorbent resin (B) is preferable to be such that 90 to 100% by weight thereof possesses particle diameters falling in the range of from 1 to 149 $\mu$m, preferably from 1 to 74 $\mu$m.

The absorbent resin (B) may be identical or not identical in composition with the monomer component (A). When the physical properties of the finally produced absorbent resin demand a due consideration and the production requires the operation of this invention to be repeated, they are preferable to be identical in composition. The method of polymerization to be employed for the production of the absorbent resin (B) may be in the form of aqueous solution polymerization or in other form of polymerization. When the possibility of the operation of this method being repeated is taken into consideration, the polymerization is preferable to be effected in the form of aqueous solution polymerization. The aforementioned polymer of an unsaturated carboxylic acid may be what has been obtained by having 0.3 to 0.9 equivalent weight, preferably 0.6 to 0.8 equivalent weight, of the carboxylic group thereof neutralized. The absorbent resin (B) of this kind may be the portion of the absorbent resin obtained by the conventional method which possesses a specific range of particle size. It may be obtained by further pulverizing a commercially available absorbent resin by the use of a pulverizing device well known to persons of ordinary skill in the art. Alternatively, from the salt-resistant absorbent resin produced by the aqueous solution polymerization in accordance with the method of this invention and then finished by the steps of drying and classification, the portion of resin (C) having the same range of particle size as the absorbent resin (B) may be used as the absorbent resin (B) in the next batch of production of the salt-resistant absorbent resin. Further, the absorbent resin (B) may be one which is treated for increasing cross-linking density at a surface region.

To produce the absorbent resin excelling particularly in salt-resistance in a high yield, the amount of the absorbent resin (B) to be used is in the range of from 1 to 30 parts by weight, preferably from 5 to 20 parts by weight, based on 100 parts by weight of the monomer component (A). If this amount exceeds 30 parts by weight, the salt-resistant absorbent resin possessing a high absorbency as desired is not obtained because the absorbent resin (B) is not uniformly dispersed in the monomer component (A) to induce thorough swelling and is consequently suffered to separate in the form of deposit. Conversely, if this amount is less than 1 part by weight, the produced absorbent resin fails to manifest the salt-resistance aimed at by this invention. Further, addition of the absorbent resin (B) into the monomer component (A) is usually carried out until polymerization of the monomer component (A) starts, but the absorbent resin (B) may be added during the system has still flowability after starting the polymerization.

In accordance with the method of this invention, the production of the salt-resistant absorbent resin is attained simply by subjecting the monomer component (A) to aqueous solution polymerization in the presence of the absorbent resin (B) without the use of a cross-linking agent presumably because the monomer component (A) polymerizes with the absorbent resin (B) while assuming a graft or IPN structure. To obtain the absorbent resin with still higher gel strength, the monomer component (A) is preferable to have a cross-linking agent incorporated therein in advance of the polymerization.

The cross-linking agents which are effectively usable for this invention in the present invention include compounds possessing at least two ethylenically unsaturated groups in the molecular unit such as ethylene glycol di(meth)acrylates, diethylene glycol di(meth)acrylates, triethylene glycol di(meth)acrylates, propylene glycol di(meth)acrylates, polyethylene glycol di(meth)acrylates, trimethylol propane tri(meth)acrylates, pentaerythritol tri(meth)acrylates, pentaerythritol di(meth)a- crylates, N,N'-methylenebis(meth)acrylamides, triallyl isocyanurate, and trimethylol propane di(meth)allyl ethers; polyhydric alcohols such as ethylene glycol, diethylene glycol, triethylene glycol, polyethylene glycol, glycerol, polyglycerol, propylene glycol, diethanol amine, triethanol amine, polypropylene glycol, polyvinyl alcohol, pentaerythritol, sorbitol, sorbitan, glucose, mannitol, monnitan, sucrose, and glucose; polyglycidyl ethers such as ethylene glycol diglycidyl ether, polyethylene glycol diglycidyl ether, and glycerol triglycidyl ether; haloepoxy compounds such as epichlorohydrin and a-methylehlorohydrin; polyaldehydes such as glutalaldehyde and glyoxal; polyamines such as ethylene diamine; hydroxides, halides, carbonates, oxides, borax and other borates of metals of Groups 2A, 3B, and 8 in the Periodic Table of Elements such as calcium hydroxide, calcium chloride, calcium carbonate, calcium oxide, magnesium chloroborax, magnesium oxide, aluminum chloride, zinc chloride, and nickel chloride; and polyvalent metal compounds such as polyvalent metal alcoholates represented by aluminum isopropylate, for example. One member or a combination of two or more members to be selected in due consideration of the reactivity from the group of cross-linking agents enumerated above may be used. It is most preferable to use, among other compounds mentioned above, a compound possessing at least two ethylenically unsaturated groups in the molecular unit thereof as the cross-linking agent.

For the cross-linking agent to manifest its necessary and sufficient effect, it is preferable to be used in an amount of from 0.001 to 0.1 mol%, preferably 0.01 to 0.05 mol%, based on the amount of the monomer component (A). It should be noted that when this amount exceeds 0.1 mol%, the excess of the cross-linking agent has the possibility of compelling the produced resin to suffer from a lowered absorbency.

For this invention, the adoption of aqueous solution polymerization as the manner of polymerization forms an indispensable requirement. If the polymerization contemplated by this invention is performed by other methods such as, for example, reversed-phase suspension polymerization, spray polymerization, and precipitation polymerization, the absorbent resin (B) cannot be stably dispersed and uniformly lodged in the monomer component (A). Thus, the effect of salt-resistance aimed at by the present invention cannot be attained.

The aqueous solution polymerization, for the purpose of enabling the absorbent resin (B) to be uniformly dispersed in the monomer component (A) and consequently causing the graft reaction to proceed efficiently, is preferably carried out in a stirred state. Thus, the polymerization is preferably carried out in a reaction vessel provided with a rotary stirring shaft. More desirably, the polymerization is carried out in a reaction vessel provided with a plurality of rotary stirring shaft so that the gel mass formed in consequence of polymerization is finely divided while the polymerization is in progress. As disclosed in JP-A-57-34,101, U.S. Pat. No. 4,625,001, and EP 0343,919, it is most preferable to use a kneader as the reaction vessel provided with a plurality of rotary stirring shafts.

For the initiation of this polymerization, the method using a radical polymerization catalyst and the method resorting to irradiation of an activated energy ray are available, for example. The radical polymerization catalysts which are effectively usable herein include peroxides such as hydrogen peroxide and benzoyl peroxide; azo compounds such as 2,2'-azobis-2-amidinopropane dihydrochloride and azobisisobutylonitrile; radical generating agents such as persulfates represented by ammonium persulfate, potassium persulfate, and sodium persulfate; and redox type initiators resulting from combination of such radical generating agents as described above with such reducing agents as sodium hydrogen sulfite, L-ascorbic acid, and ferrous salts, for example. The amount of the radical polymerization catalyst to be used is in the range of from 0.01 to 0.5 % by weight, preferably from 0.05 to 0.3 % by weight, based on the amount of the monomer component (A). For the aqueous solution polymerization, it is desirable to use water alone as the polymerization medium. This water, when necessary, may incorporate therein such a hydrophilic organic solvent as methanol, ethanol, acetone, dimethyl formaldehyde, or dimethyl sulfoxide.

Though the concentration of the monomer component (A) in the aqueous solution polymerization system is not particularly restricted but may be selected from a wide range, the ratio of the monomer component (A) to the water is preferable to fall in the range of 1:9 to 7:3 (by weight), especially 3:7 to 5:5 in due consideration of the ease of control of the polymerization reaction and the yield of the reaction.

The term "salt-resistance" as used in this invention means that the degree of change in the absorbency as to the salt concentration of the aqueous solution subjected to absorption is small. Hence, the salt-resistance is defined to be the quotient of the absorbency of physiological saline solution/the absorbency of deionized water.

When the absorbent resin possessing improved salt-resistance is used as the absorbent in such a sanitary article as disposable diaper, for example, it hardly yields to the influence of the salt concentration in urine, retains a stable absorbency, and excels in the ability to absorb body fluid. When it is used in a sealing material to repel seawater, it enjoys the advantage that the sealing effect of the material is affected less easily by the salt concentration.

Now, the present invention will be described more specifically below with reference to working examples. It should be noted that the scope of this invention is not limited in any sense by these working examples.

The absorbency and the gel strength of a given salt-resistant absorbent resin were determined by the following methods.

(1) Absorbency of deionized water: About 0.05 g of a sample salt-resistant absorbent resin was uniformly placed in a teabag-like pouch of non-woven fabric (40 mm $\times$ 150 mm), immersed in a large excess of deionized water for 30 minutes, removed from the deionized water and left draining on a paper, and weighed to find the amount of deionized water absorbed thereby. An empty teabag-like pouch itself was caused to absorb the deionized water by following the same procedure and the weight of the wet pouch was found as a blank. Absorbency of deionized water was calculated in accordance with the following formula.

Absorbency of deionized water (g/g) = (Weight after absorption, g — Blank, g)/(Weight of salt-resistant absorbent resin, g)

(2) Absorbency of physiological saline solution: About 0.2 g of a sample salt-resistant absorbent resin was uniformly placed in a teabag-like pouch of non-woven fabric (40 mm $\times$ 150 mm), immersed in a large excess of physiological saline solution (0.9 weight% NaCl) for 30 minutes, removed from the solution and left draining on a paper, and weighed to find the amount of the solution absorbed thereby. An empty teabag-like pouch itself was caused to absorb the physiological saline solution by following the same procedure and the weight of the wet pouch was found as a blank. Absorbency of physiological saline solution was calculated in accordance with the following formula.

Absorbency of physiological saline solution (g/g) = (Weight after absorption, g—Blank, g)/(Weight of salt-resistant absorbent resin, g)

The salt-resistance was expressed by the quotient, (Absorbency of physiological saline solution)/(Absorbency of deionized water).

(3) Gel strength: A given sample in the form of swelled hydrogel was tested for gel strength by the use of a stress rheometer provided with a disc 2.5 cm in radius under the conditions of 0.1 em in sample thickness and 1.0 Hz in frequency of vibration. The modulus of shear elasticity thus found of the swelled hydrogel was reported as the gel strength. The swelled hydrogel was obtained by allowing a given salt-resistant absorbent resin to be swelled with synthetic urine (comprising 1.9% by weight of urea, 0.8% by weight of NaCl, 0.1% by weight of $CaCl_2$, and 0.1% by weight of $MgSO_4$) for one hour and then deprived of excess synthetic urine with filter paper.

EXAMPLE 1

In a jacketed stainless steel twin-arm kneader having an inner volume of 10 liters and provided with two sigma type vanes 120 mm in radius of rotation, 4,400 g of an aqueous solution of a monomer component (A) (monomer component concentration 37% by weight) comprising of 75 mol% of sodium acrylate and 25 mol% of acrylic acid and 2.72 g (0.05 mol% based on monomer component (A)) of trimethylol propane triacrylate as a cross-linking agent were placed and nitrogen gas was blown in to displace the gas entrapped in the reaction system. Then, the monomer component (A) and the cross-linking agent were stirred by the rotation of the two sigma type vanes and, at the same time, 162 g ( 10% by weight based on the amount of monomer component (A)) of an absorbent resin (B) having particle diameters of from 1 to 149 μm and resulting from pulverizing an absorbent resin (produced by Nippon Shokubai Kagaku Kogyo Co., Ltd. and marketed under trademark designation of "Aqualic CA") with a hammer mill and passing the resultant powder was added to the stirred mixture. The reaction system was heated by passing hot water at 30° C. through the jacket and 1.10 g of sodium persulfate and 1.10 g of sodium hydrogen sulfite were added as initiators to the heated reaction system. The polymerization reaction was initiated and further continued for 60 minutes. The gel polymer consequently obtained was in the form of finely divided particles about 3 mm in diameter. On a metallic gauze, the gel polymer was dried with hot air at a temperature of 150° C. for two hours. The dried polymer was pulverized with a hammer mill, to obtain a salt-resistant absorbent resin. The properties of the salt-resistant absorbent resin are shown in Table 1.

EXAMPLE 2

A salt-resistant absorbent resin was obtained by following the procedure of Example 1, except that the amount of the absorbent resin (B) was changed to 407 g (25% by weight based on the monomer component (A)). The properties of the salt-resistant absorbent resin are shown in Table 1.

EXAMPLE 3

A salt-resistant absorbent resin was obtained by following the procedure of Example 2, except that the use of the cross-linking agent was omitted. The properties of the salt-resistant absorbent resin are shown in Table 1.

EXAMPLE 4

In the same twin arm kneader as used in Example 1, 2,490 g of an aqueous solution of a monomer component (A) (monomer component concentration 40% by weight) comprising of 108 g of acrylic acid, 282 g of sodium acrylate, and 606 g of sodium sulfoethyl acrylate and 0.888 g (0.04 mol% based on monomer component (A)) of trimethylol propane triacrylate as a cross-linking agent were placed and nitrogen gas was blown in to displace the gas entrapped in the reaction system with nitrogen. Then, the monomer component and the cross-linking agent were stirred by the rotation of the two sigma type vanes and 97 g (10% by weight based on the monomer component (A) ) of the same absorbent resin (B) as used in Example 1 was added to the stirred mixture. The reaction system was heated by passing hot water at 30° C. through the jacket and 0. 9 g of ammonium persulfate and 0.038 g of L-ascorbic acid were added as polymerization initiator to the heated reaction system. The polymerization reaction which was consequently initiated and further continued for 90 minutes. The gel polymer thus obtained was in the form of finely divided particles about 3 mm in diameter. The resultant gel polymer was dried with hot air at a temperature of 150° C. for two hours. The dried polymer was pulverized with a hammer mill, to obtain a salt-resistant absorbent resin. The properties of this salt-resistant absorbent resin are shown in Table 1.

EXAMPLE 5

A salt-resistant absorbent resin was obtained by following the procedure of Example 4, except that the use of the cross-linking agent was omitted. The properties of the salt-resistant absorbent resin are shown in Table 1.

EXAMPLE 6

A salt-resistant absorbent resin was obtained by following the procedure of Example 4, except that the amount of the absorbent resin (B) was changed to 49.8 g (5% by weight based on the monomer component (A) ). The properties of the salt-resistant absorbent resin are shown in Table 1.

EXAMPLE 7

A salt-resistant absorbent resin was obtained by following the procedure of Example 1, except that the absorbent resin (B) was a powder passed through a metallic gauze of 20 mesh and possessed of particle diameters of from 1 to 840 μm. The properties of this salt-resistant absorbent resin are shown in Table 1.

CONTROL 1

A resin for comparison was obtained by following the procedure of Example 1, except that the amount of the absorbent resin (B) was changed to 3,256 g (50% by weight based on the monomer component (A)). The properties of this resin for comparison are shown in Table 1.

CONTROL 2

A resin for comparison was obtained by following the procedure of Example 1, except that the use of the absorbent resin (B) was omitted. The properties of the resin for comparison are shown in Table 1.

CONTROL 3

A resin for comparison was obtained by following the procedure of Example 1, except that the amount of the cross-linking agent was changed to 27.2 g (0.5 mol% based on the monomer component (A)) and the use of the absorbent resin (B) was omitted. The properties of this resin for comparison are shown in Table 1.

CONTROL 4

In an atmosphere of nitrogen, 20 parts of polyethylene oxide resin thoroughly dehydrated by the vacuum drying method and possessing an average molecular weight of 100,000 and 0.05 part of triethylene diamine were thoroughly dissolved in 280 parts of acetonitrile at temperatures of from 30° C. to 40° C. Then, the resultant solution and 0.2 part of 1,4-phenylene diisocyanate added thereto were left reacting at 70° C. for five hours, to obtain a homogeneous resin solution insoluble in water. The reaction product was cast in a petri dish of glass, vacuum dried at 40° C., and then pulverized, to obtain a resin for comparison. The properties of the resin for comparison are shown in Table 1.

CONTROL 5

A resin for comparison was obtained by following the procedure of Example 3, except that the use of the absorbent resin (B) was omitted. The properties of the resin for comparison are shown in Table 1.

CONTROL 6

A four-necked separable flask having an inner volume of 2 liters and provided with a stirrer, a reflux condenser, a thermometer, a nitrogen gas inlet tube, and a dropping funnel, 1.0 liter of cyclohexane was placed, 3.0 g of sorbitan monostearate as a dispersant was added thereto and dissolved therein, and nitrogen gas was blown in to expel the dissolved oxygen.

Separately, 84.6 g of sodium acrylate, 21.6 g of acrylic acid, and 0.0925 g (0.05 mol% based on the monomer component (A)) of N,N'-methylenebisacrylamide as a cross-linking agent were dissolved in 197 g of deionized water. The resultant aqueous solution and 10.6 g (10% by weight based on the monomer component (A)) of the same absorbent resin (B) as used in Example 1 added thereto were combined.

In this aqueous solution of the monomer component, 0.15 g of potassium persulfate was dissolved and then nitrogen gas was brown in to expel the dissolved oxygen therefrom.

Then, the aqueous solution of the monomer component prepared in the flask was transferred to the aforementioned separable flask and stirred to be dispersed. Thereafter, the bath temperature was elevated to 65° C. to initiate polymerization reaction of the aqueous solution and held at this temperature for two hours to complete the polymerization. The hydrogel obtained in consequence of the polymerization was distilled to expel the contained water and cyclohexane through azeotropic dehydration. This polymer was filtered to obtain a resin for comparison.

TABLE 1

| Example | Absorbency (g/g) | | Salt resistance (—) | Gel strength (dyne/cm$^2$) |
|---|---|---|---|---|
| | Deionized water | Physiological saline solation | | |
| 1 | 139 | 43 | 0.31 | 28000 |
| 2 | 125 | 40 | 0.32 | 30000 |
| 3 | 127 | 42 | 0.33 | 25000 |
| 4 | 85 | 34 | 0.40 | 32000 |
| 5 | 105 | 40 | 0.38 | 28000 |
| 6 | 113 | 42 | 0.37 | 23000 |
| 7 | 146 | 38 | 0.26 | 24000 |
| Control 1 | 120 | 21 | 0.18 | 34000 |
| Control 2 | 310 | 43 | 0.14 | 17000 |
| Control 3 | 130 | 21 | 0.16 | 23000 |
| Control 4 | 14 | 10 | 0.71 | — |
| Control 5 | almost dissolution | almost dissolution | — | — |
| Control 6 | 380 | 46 | 0.12 | 16000 |

What is claimed is:

1. A method for the production of a salt-resistant absorbent resin, which comprises
   preparing an aqueous dispersion comprising an absorbent resin (B) which is water-insoluble and capable of forming a hydrated gel on absorption of water and at least one monomer component (A) selected from the group consisting of unsaturated polymerizable carboxylic acids and salts thereof, wherein the ratio of the absorbent resin (B) is from 1 to 30 parts by weight, based on 100 parts by weight of said monomer component (A):
   subjecting the aqueous dispersion to aqueous solution polymerization to provide a polymer gel; and
   drying the polymer gel.

2. A method according to claim 1, wherein said aqueous solution polymerization is carried out with the reactants kept in a stirred state.

3. A method according to claim 2, wherein said aqueous solution polymerization is carried out in a stirred state within a reaction vessel provided with a plurality of rotary stirring shafts.

4. A method according to claim 3, wherein said reaction vessel provided with a plurality of rotary stirring shafts is a kneader.

5. A method according to claim 1, wherein a cross-linking agent is used in an amount of from 0.001 to 0.1 mol% based on the amount of said monomer component (A).

6. A method according to claim 1, wherein said aqueous solution polymerization is carried out in the presence of from 5 to 20 parts by weight of said absorbent resin (B), based on 100 parts by weight of said monomer component (A).

7. A method according to claim 1, wherein the water content of said absorbent resin (B) is in the range of from 0.1 to 10% by weight.

8. A method according to claim 1, wherein 90 to 100% by weight of said absorbent resin (B) has particle diameters of from 1 to 149 μm.

9. A method according to claim 1, wherein said absorbent resin (B) has been produced by aqueous solution polymerization.

10. A method according to claim 1, wherein said absorbent resin (B) has been obtained by polymerizing said monomer component (A).

11. A method according to claim 1, wherein said monomer component (A) is at least one member selected from the group consisting of (meth)acrylic acids, crotonic acid, itaconic acid, maleic acid, fumaric acid, citraconic acid, and salts thereof.

12. A method according to claim 1, wherein said monomer component (A) is at least one member selected from the group consisting of acrylic acid and salts thereof.

13. A method according to claim 12, wherein said monomer component comprises 10 to 70 mol% of acrylic acid and 90 to 30 mol% of acrylic acid salts.

14. A method according to claim 13, wherein a cross-linking agent is contained in an amount of from 0.001 to 0.1 mol% based on the amount of said monomer component (A).

15. A method according to claim 1, wherein said absorbent resin (B) is a cross-linked partially neutralized acrylate polymer.

16. A method according to claim 1, wherein said absorbent resin (B) has been obtained by subjecting the monomer component (A) recited in claim 14 to aqueous solution polymerization.

17. A method according to claim 15, wherein said absorbent resin (B) is a cross-linked polymer of a monomer component containing 0.001 to 0.1 mol% of a cross-linking agent and neutralizing from 0.3 to 0.9 equivalent weight of the carboxyl group of an acrylic acid.

18. A method according to claim 1, wherein said hydrated absorbent resin resulting from said aqueous solution polymerization is dried and then classified to be deprived of an absorbent resin (C) possessing the same range of particle size as said absorbent resin (B).

19. A method according to claim 1, wherein a polymerization initiator is added to said dispersion prior to subjecting said aqueous dispersion to aqueous solution polymerization.

20. A method according to claim 1, wherein said polymer gel is heated to dry the gel.

* * * * *